United States Patent [19]
Chirila et al.

[11] Patent Number: 5,252,628
[45] Date of Patent: Oct. 12, 1993

[54] METHOD OF MAKING PHOTOPROTECTIVE HYDROPHILIC POLYMERS AND OCULAR DEVICES THEREOF

[75] Inventors: Traian V. Chirila, Hillarys; Ian J. Constable, Mosman Park; Richard L. Cooper, Mount Claremont, all of Australia

[73] Assignee: Lions Eye Institute of Western Australia, Inc.

[21] Appl. No.: 447,885

[22] Filed: Dec. 7, 1989

[51] Int. Cl.$^5$ .................. B29D 11/00; C08F 20/28; F21V 9/00
[52] U.S. Cl. .................. 523/106; 351/160 H; 524/240; 524/916; 525/328.8; 525/380; 525/903; 623/6
[58] Field of Search .......... 523/106; 351/160 H; 623/6; 524/240, 916; 525/328.8, 380, 903

[56] References Cited

U.S. PATENT DOCUMENTS

| | | | |
|---|---|---|---|
| 3,476,499 | 11/1969 | Wicherie | 8/507 |
| 3,679,504 | 7/1972 | Wicherie | 156/62 |
| 4,157,892 | 6/1979 | Tanaka et al. | 8/14 |
| 4,252,421 | 2/1981 | Foley, Jr. | 351/162 |
| 4,310,650 | 1/1982 | Gupta et al. | 526/313 |
| 4,390,676 | 6/1983 | Loshaek | 526/313 |
| 4,528,311 | 7/1985 | Beard et al. | 524/91 |
| 4,559,056 | 12/1985 | Su | 8/507 |
| 4,668,506 | 5/1987 | Bawa | 424/429 |
| 4,808,709 | 2/1989 | Onishi | 523/106 |
| 5,112,883 | 5/1992 | Gallas | 523/106 |

FOREIGN PATENT DOCUMENTS

WO8901639 2/1989 PCT Int'l Appl.

Primary Examiner—Paul R. Michl
Assistant Examiner—Andrew E. C. Merriam
Attorney, Agent, or Firm—Walter H. Dreger

[57] ABSTRACT

A method of making pigmented hydrophilic polymers in such a manner that the resulting polymers absorb ultraviolet and visible radiation, and that no migration, separation or leaching of the pigment can take place, is disclosed. The polymer compositions comprise blends of hydrophilic polymers with melanin pigments, the latter being synthesized on the hydrophilic polymer matrix. The disclosed polymer compositions are useful in the manufacture of ocular devices, particularly intraocular lenses and aphakic contact lenses capable of absorbing ultraviolet and visible radiation, at wavelengths between 300 and 700 nanometers, to the same extent as the natural crystalline lens of the eye. The disclosed method is also useful to impart photoprotective properties to the already made said ocular devices.

16 Claims, 9 Drawing Sheets

Example 4

Example 4

Fig.6 Example 6

Example 11

METHOD OF MAKING PHOTOPROTECTIVE HYDROPHILIC POLYMERS AND OCULAR DEVICES THEREOF

BACKGROUND OF THE INVENTION

People with their natural lens (crystalline lens) of the eye opacified as a result of cataractogenesis require surgical removal of the diseased lens. This condition, known as aphakia, is incompatible with normal vision due to gross anomalies of the refraction and accommodation caused by the absence of the lens in the dioptric system of the eye, and must be corrected. Correction may be achieved by spectacle or contact high plus lenses, by surgical insertion of an artificial plastic lens in the eye as a substitute for the removed crystalline lens, and by surgical modification of the cornea (keratoplasty and epikeratoplasty).

The spectacle corrective lenses, known as cataract glasses, cannot correct monocular aphakia and have also many other drawbacks (loss of visual field with induced ring scotoma, spherical aberration, distortion, magnifying effect, they are cosmetically undesirable). Correction of aphakia through corneal surgery is still limited to investigative conditions. The remaining two procedures, contact lens and artificial intraocular lens, have become presently the best ways for rehabilitation of the cataract patients. It is to be noted that the main use of contact lenses is for correction of vision in the phakic persons wherefore they are thinner than those intended as corrective lenses for the aphakic persons. Both contact and intraocular lenses are currently manufactured from polymeric materials, either hard, generally poly(methyl methacrylate), or soft, when the materials are water-swellable hydrogels of an acrylic or non-acrylic nature, or various hydrophobic flexible polymers. This invention relates to soft hydrophilic materials for the manufacture of both corrective contact lenses for the aphakic patients, and artificial intraocular lenses.

A significant portion of the non-ionizing electromagnetic radiation emanating from the sun, which encompasses ultraviolet (100 to 400 nanometers wavelength), visible (400 to 780 nanometers) and infrared (780 nanometers to 1 millimeter) regions, is potentially harmful to the structural components of the eye, especially to the retina, through thermal and photochemical processes. Except for the cornea which is exposed to the whole atmospheric radiation, that is only from 285 nanometers onwards since the radiation below this wavelength is absorbed by the ozone layer, the other segments of the eye are progressively and selectively protected by the absorbing action of the preceding tissues. The eye therefore appears not only as a complex hydrodynamic system which assures the stability and regulation of the intraocular pressure, and not only as a perfect dioptric system producing a detailed image on the retina, but also as a proper filtering system consisting of a consecutive series of filters which ultimately protect the retina against the harmful effects of certain radiation wavelengths. As a result the human retina in its adult stage is exposed exclusively to radiation wavelengths between 400 and 1400 nanometers, since the remaining incident radiation is absorbed by the cornea, aqueous humor, crystalline lens and vitreous body.

The natural lens is an essential component of the filtering system. From age twenty on, the crystalline lens absorbs most of the ultraviolet radiation between 300 and 400 nanometers, a region known as UV-A. Absorption is enhanced and shifted to longer wavelengths as the lens grows older and it expands eventually over the whole visible region. This phenomenon is correlated with the natural production of fluorescent chromophores in the lens and their age-dependent increasing concentration. Concomitantly, the lens turns yellower due to generation of certain pigments by the continuous photodegradation of the molecules which absorb in the UV-A region. This progressive pigmentation is responsible for the linear decrease in transmission of visible light, since the almost complete absorption in the UV-A region remains constant after age twenty-five.

The damaging effects of intense natural light to the retina, especially of the long-wavelength ultraviolet radiation (UV-A, 300 to 400 nanometers) and short-wavelength visible radiation (400 to 510 nanometers) were noticed some time ago. The acute ultraviolet hazards apply when the eye is exposed to excessive amounts of radiation. These hazards, occurring commonly in certain industrial environments, are well recognized and prevented by the use of regulated or standardized protection equipment. Similarly, the eye is protected from acute injury of the visible radiation by involuntary aversion reflexes of the eye itself, as blinking. However, more subtle photochemical effects induced by the daily exposure to relatively low levels of UV-A radiation and visible radiation at the violet/blue end of the spectrum have been appreciated recently and they are of a greater concern. The retina is very vulnerable to UV-A radiation and the damage inflicted is extensive, as demonstrated on experimental animals. The sensitivity of the retina to short-wavelength visible radiation, known as 'blue light hazard region', is lower but this radiation is ubiquitous and reaches the eye unhampered during the entire diurnal life. Both UV-A radiation and blue light are linked with the age-related degeneration of the retina, as described in: Kirkness, C. M. and Weale, R. A., Transactions of the Ophthalmological Societies of the United Kingdom, vol. 104, pp. 699-702 (1985), "Does Light Pose a Hazard to the Macula in Aphakia ?"; Marshall, J., Ophthalmic and Physiological Optics, vol. 5, pp. 241-263 (1985), "Radiation and the ageing eye"; Mainster, M. A., Eye, vol. 1, pp. 304-310 (1987), "Light and Macular Degeneration: A Biophysical and Clinical Perspective"; and Young, R. W., Survey of Ophthalmology, vol. 32, pp. 252-269 (1988), "Solar Radiation and Age-related Macular Degeneration". The experimental evidence, at least for the blue light hazard, is compelling, and the specialists recommend adequate protection by filtering off as much as possible radiation from 300 to 510 nanometers. This is precisely the work performed by the adult natural lens as part of the filtering system of the eye. In the aphakic eye the most important filter in this system is therefore lost and the age-compromised retina is suddenly exposed to a large dose of harmful radiation.

It is clear that any artificial ocular device intended to act as a substitute for the natural lens must duplicate its filtering properties. Therefore, the materials used to manufacture corrective contact lenses and intraocular lenses should possess adsorptive characteristics matching those of the natural lens.

It is the prime object of this invention to provide a method for obtaining hydrophilic polymers capable of absorbing visible radiation to the same extent as the natural lens. When ultraviolet absorbing agents known in the art are incorporated, the procedure will allow for hydrophilic polymers to be produced which mimic the radiation-absorptive, hence photoprotective properties of the human natural lens. This invention further relates to ocular devices for correction of aphakia, particularly soft intraocular lenses and soft contact lenses, which are made from these polymers.

PRIOR ART

Radiation-absorbing agents, including the best known particular case of coloring agents (dyes and pigments) which absorb visible radiation, have been incorporated in polymeric materials for a long time with the purpose to render the polymers absorbent in certain regions of the sun radiation such as near ultraviolet (300 to 400 nanometers), some wavebands in the visible region, and near infrared (800 to 5000 nanometers), or simply for obtaining colored plastic materials. Known methods of incorporating these agents include the following:

A. Physical incorporation of agents in polymers, which includes:

A.1. The agent, either an organic dye, an absorbing compound, an inorganic pigment, or a fine mineral powder of reflective particles, is dispersed or dissolved in the required monomer mixture which is then subjected to polymerization, as disclosed, for example, in U.S. Pat. Nos. 2,477,462; 2,500,023; 3,189,914; 4,252,421; 4,278,589; 4,278,590; 4,304,895; 4,390,676; 4,460,523; 4,472,327; 4,615,593 and 4,702,574, and in Brit. Pat. No. 920,390.

A.2. The agent, either an organic dye, an absorbing compound, an inorganic pigment, or a fine mineral powder is mixed and dispersed into the required polymer by blending techniques, such as hot roll-milling, as disclosed, for example, in U.S. Pat. No. 3,382,183.

A.3. The agent, preferably an organic dye or absorbing compound, is dissolved in a suitable solvent. The solution is then mixed with a solution of the required polymer in a solvent miscible with the first one. On evaporating the solvents, a solid polymer composition containing the agent is obtained. This procedure is disclosed, for example, in U.S. Pat. No. 2,043,860, and in Fr. Patents Nos. 1,324,897 and 1,324,898.

A.4. The agent, preferably an organic dye or absorbing compound, is dissolved in a suitable solvent. The required polymer is immersed in the solution which permeates into the polymer up to a depth dependent upon the duration of immersion. This procedure is disclosed, for example, in U.S. Pat. Nos. 2,038,114; 2,062,179; 2,129,131; 2,129,132; 2,364,112; 3,297,462; 3,382,183; 4,494,954; 4,702,574, and 4,707,236, and in Ger. Pat. No. 802,613 as well as in Newcomer, P. C. and Janoff, L. E., American Journal of Optometry and Physiological Optics, vol. 54, pp. 160–164 (1977), "Methods of Tinting Soflens ® Contact Lenses".

A variation of this procedure, preferably applicable for inorganic pigments is featured by the penetration into polymer from opposite directions of two solutions of different compounds. When they come into contact, a colored layer is produced as a result of chemical reactions. This procedure is disclosed, for example, in U.S. Pat. Nos. 3,476,499 and 4,576,453.

A.5. A precursor of the agent, preferably an azoic and any vat dye as such or in its leuco form, is dissolved in water, and the required polymer, preferably a hydrophillic polymer, is immersed into solution. The solution permeates into the polymer which subsequently is treated with a developing agent to generate color as a result of chemical reactions such as coupling, precipitation or photolysis. This procedure is disclosed, for example, in U.S. Pat. Nos. 2,138,553; 4,634,449 and 4,719,657, and in Eur. Pat. Appl. No. 122,771; Ger. Pat. No. 2,728,613; Brit. Pat. No. 1,547,525; Australian Pat. No. 226,210 and Australian Pat. Abridg. No. AU-B-26340/84.

B. Surface treatment techniques, which include:

B.1. Offset printing with ink type coloring agents, as disclosed, for example, in U.S. Pat. No. 4,582,402, and in Jap. Pat. No. 78,128,667.

B.2. The agent, preferably an organic dye or absorbing compound, is dissolved in a suitable solvent. The required polymer is coated with this solution by dipping, brushing or spraying. After evaporation, a colored or radiation-absorbing film covers the polymer surface. This procedure is disclosed, for example, in U.S. Pat. Nos. 2,038,114; 2,043,860; 2,062,179; 2,129.131; 2,128,132; 2,364,112 and 3,519,462.

B.3. Insertion of a layer of coloring or absorbing agent between two layers of the same polymer or two different polymers, as a result of successive polymerization processes, as disclosed, for example, in U.S. Pat. No. 3,679,504.

C. Chemical incorporation of agents in polymers, which includes:

C.1. Chemical inclusion in the polymer chain of pendant reactive organic functional groups which subsequently are transformed, by chemical reaction with suitable agents, into color-producing or radiation-absorbing structural moieties. This method has been used preferably for azoic dyes in two variations: (a) a polymer containing coupling groups was coupled with diazonium salts, and (b) a polymer was firstly diazotized and then coupled, as both disclosed, for example, in U.S. Pat. Nos. 1,500,844; 1,886,480; 2,477,462 and 3,304,297.

The procedure is also applicable to non-azoic dyes, as disclosed, for example, in U.S. Pat. Nos. 1,886,480; 2,477,462; 4,468,229; 4,553,975 and 4,559,059.

C.2. The agent, usually an organic dye or absorbing compound, is a polyfunctional reactive compound, therefore polymerizable or polycondensable. Consequently, it can be used as a comonomer, which after having been mixed with the required monomers, is subjected to addition or condensation polymerization resulting in copolymers containing bonded repetitive coloring or absorbing chromophores. This procedure is disclosed, for example, in U.S. Pat. Nos. 3,133,042; 3,173,893; 3,215,665; 3,272,891; 3,278,486; 3,320,116; 3,341,493; 3,344,098; 3,399,173; 3,467,642; 3,493,539; 4,157,892; 4,233,430; 4,252,421; 4,304,895; 4,310,650; 4,390,676; 4,468,229; 4,528,311; 4,553,975 and 4,559,059, and in Brit. Pat. No. 885,986 and Fr. Pat. No. 2,237,912.

In a slightly different modification of this procedure, the monomeric coloring or absorbing agent is homopolymerized, and the resulting polymer is incorporated into the required polymer by blending techniques or dissolved and used as a coating for the required polymer, as disclosed, for example, in U.S. Pat. Nos. 3,133,042; 3,272,891; 3,313,866 and 3,320,116, and in Eur. Pat. Appl. No. 10,518 and Belg. Pat. No. 629,109.

The purpose of the aforementioned inventions included mainly the production of colored polymers for the manufacture of various commodities, and the improvement of light stability of the polymeric materials to be used in outdoor conditions. In the art of ocular devices, the tinting of contact lenses have been a well known practice, used for: (a) cosmetic purposes, either to enhance or change color of the eyes, or to conceal disfiguring conditions of the anterior segment; (b) therapeutic occluding; (c) aiding wearers in handling the lenses with reduced loss or damage, and (d) protection against bright light for patients with anomalous sensitivity. The tinted contact lenses have some drawbacks including the potential toxicity of the dyeing agents and their metabolic degradation products, and the worsening of dark adaptation of the wearers. More important, especially for aphakic wearers, the tinting does not usually provide protection for retina against harmful UV-A radiation and blue light. A deep tint enhances slightly the photoprotection at the expense of a higher danger of releasing toxic agents by leaching and of the impairment of dark vision. Regarding the absorption of harmful radiation, the aphakic eye fitted with a clear or lightly tinted contact lens is identical to the aphakic eye in which the cornea provides the only protective filter.

The physical incorporation of non-bonded coloring agents in hydrogel contact lenses, as disclosed, for example, in U.S. Pat. Nos. 3,476,499; 3,679,504; 4,157,892; 4,472,327; 4,576,453; 4,615,593; 4,634,449; 4,702,574 and 4,707,236, and in Eur. Pat. Appl. No. 122,771; Brit. Pat. No. 1,547,525, and Australian Pat. Abridg. No. AU-B-26340/84, has been proposed for cosmetic rather than photoprotective purposes. The extractability in aqueous media of the coloring agents resulting in their release into the eye provides a limitation of the procedure.

The use of chemical incorporation of reactive agents bonded to the polymer structure eliminates the danger of toxic release.

U.S. Pat. No. 4,252,421 discloses a method for preparation of soft hydrogel contact lenses having a colored central core. The core is obtained by copolymerizing 2-hydroxyethyl methacrylate and other acrylic comonomers with polymerizable silicon phthalocyanine dyes. These dyes have a complicated structure and they are difficult to produce. The object of the invention was to make tinted contact lenses. Photoprotection was not within the scope of the invention.

U.S. Pat. No. 4,559,059 discloses a method for preparation of soft hydrogel contact lenses, which are totally or partially colored by the chemical bonding of fibre-reactive dyes. This is achieved by the simple contact of the hydrogel lens with mildly alkaline solutions of the dyes. The main purpose of the invention was to obtain tinted contact lenses, however it was also suggested as an advantage that the said lenses could absorb ultraviolet radiation.

U.S. Pat. No. 4,390,676 discloses a method for preparation of hard and soft acrylic aphakic contact lenses containing chemically bonded bezophenone-type ultraviolet absorbers, as comonomers. Depending on the particular benzophenone derivative used, the lenses produced had cut-off wavelengths between 340 and 390 nanometers. Common visible radiation absorbers were also added in order to prevent uncomfortable vision and poor color perception caused by excessive light brightness. Since these dyes are not chemically bonded, the possibility of leaching out from the lens into the eye is not obviated. Although initially mentioned as an embodiment of the invention, the intraocular lenses have been later disclaimed (Disclaimer filed Apr. 5, 1984).

U.S. Pat. No. 4,528,311 discloses a method for preparation of hard acrylic aphakic contact lenses and intracular lenses containing chemically bonded benzo- triazole-type ultraviolet absorbers, as comonomers. The cut-off wavelength is sharp above 400 nanometres. No visible light absorber is added; on the contrary, the steepness of the absorption curve is considered an advantage since avoiding any absorption in the visible range, therefore the yellowing of the lenses. Obviously, these lenses do not provide any protection against harmful blue light.

SUMMARY OF THE INVENTION

It is the prime object of this invention to provide a new method for the production of hydrophilic, water-swelling polymers capable of absorbing radiation in the visible region of the natural spectrum.

It is another object of this invention to provide hydrophilic plastic materials for the manufacture of soft intraocular lenses and aphakic contact lenses with radiation-absorbing characteristics which mimic to a high degree the filtering characteristics of the natural human lens. Various ultraviolet-absorbing agents are suitable for the use in the present invention, in conjunction with the method constituting the aforementioned prime object of this invention. Except in combination in the filtering systems of this invention, the particular ultraviolet-absorbing agent or agents per se do not constitute a part of this invention.

A still further object of the present invention is to provide a method for imparting absorptive characteristics in the visible region of the natural spectrum to intraocular lenses and aphakic lenses which are already available on the market, or kept in inventory, or have been prescribed to the patient.

Briefly stated, the method of the present invention comprises the in vitro synthesis of melanin-like organic pigments within the network of hydrophilic polymers. Chemically, the process consists of the oxidative polymerization in solution, induced by oxygen and light, with or without catalytic assistance from specific enzymes, of 4-hydroxyphenylethylamines, henceforth designated as tyrosine and related compounds, and 3,4-dihyroxyphenylethylamines, henceforth designated as catecholamines, on the macromolecular matrix of the hydrophilic polymers. The resulting blends, which can be formally regarded as sequential interpenetrating polymer networks, are transparent materials which exhibit significant absorption of radiation wavebands known to be harmful to the retina.

In view of the complicated methods generally employed in the art, this method is superior to other known methods because it can produce radiation-absorbing hydrophillic polymer in a very simple manner. The ocular devices of the present invention possess the following advantages:

(1) Intraocular lenses and aphakic contact lenses which appear slightly yellow and absorb potentially harmful radiation between 300 and 700 nanometers to the same extent as the natural lens.

(2) The absorbing agents do not bleed or leach from the ocular devices into the eye, and they are impervious to autoclaving.

(3) The absorbing agent particles are not individually discernible to the naked eye.

(4) The ocular devices will retain their absorptive characteristics despite aging or periodical sterilization.

(5) The ocular devices can be completely manufactured by incorporating the teachings of the present invention with conventional techniques for the manufacture of intraocular lenses and contact lenses, thereby eliminating the need for additional equipment.

In view of the foregoing discussion, this invention will be more fully described by consideration of:
1. The method;
2. The substrates.

DESCRIPTION OF DRAWINGS

The invention will be also illustrated in conjunction with the accompanying drawings in which.

DETAILED DESCRIPTION

1. The Method

Figure 1:
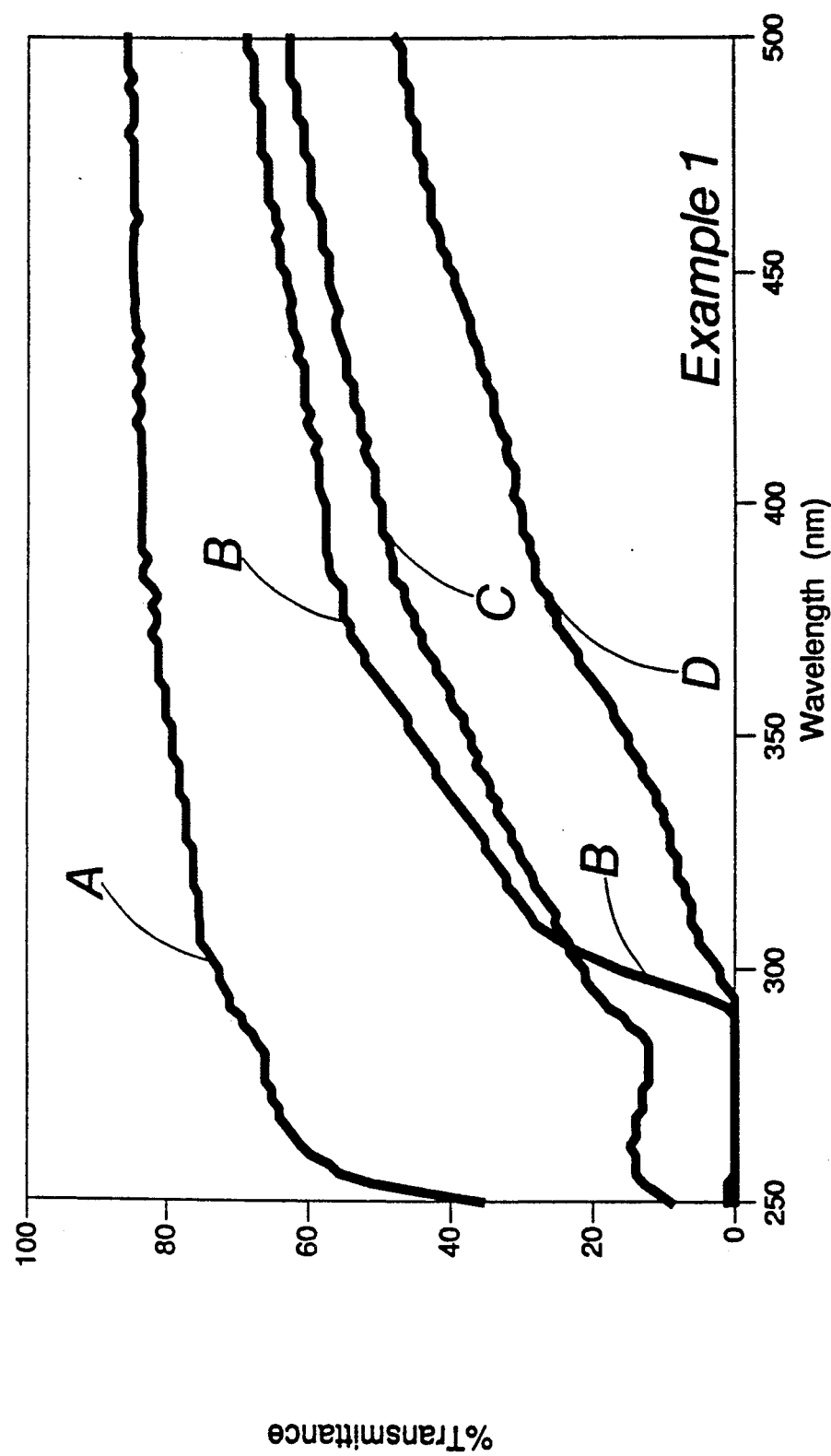
FIG. 1 is a plot of transmittance for the polymer compositions of Example 1.

Melanins are insoluble biopolymers responsible for black and some brown, red and yellow pigmentation in animals and certain plants. They are the only biochromes widely present in mammals, including the humans. The present knowledge of the melanin chemistry is rather limited because of extreme difficulties in studying them by conventional analytical techniques. Broadly, the mammalian melanins can be regarded as polymers of the indole-5,6-quinone, crosslinked to a small degree, and bound to proteins. It is known that in vivo melanogenesis proceeds through the enzymatic oxidation of tyrosine and dopa followed by the polymerization of the resulting indole-5,6-quinone derivatives. The latter process takes place on a protein matrix. It was later noticed that some derivatives of phenylethylamine, such as tyrosine and related compounds, and catecholamines can undergo, in certain conditions, in vitro melanogenesis through oxidative polymerization induced by oxygen (air) and light at room temperature. Synthetic melanins are not entirely identical to the natural ones, however both absorb strongly in the ultraviolet and visible regions of the sun radiation.

We have discovered now that polymerization to melanins of either tyrosine and related compounds, or catecholamines, henceforth also designated as melanin precursors, can proceed on the matrix of hydrophillic polymers, henceforth designated as hydrogels. The resulting polymer blends fulfil the formal prerequisites as to be defined 'sequential gradient interpenetrating polymer networks'. In this case, Polymer I is a crosslinked hydrogel, fully synthesized prior to making the blend. Monomer II is not tyrosine or a catecholamine, but a reactive indole-5,6-quinone: tyrosine or catecholamines are firstly oxidized to their corresponding aminochromes which readily rearrange to 5,6-dihydroxyindoles which are oxidized to indole-5,6-quinones. Aminochromes are soluble in water and their solutions imbibe the hydrogel. The rearrangement of aminochromes and the subsequent polymerization of indole-5,6-quinones occur then on the matrix of the Polymer I, as well as in the surrounding solution. The melanins are thus produced inside the hydrogel network and a certain interpenetration of the two networks must be involved at least at a superamolecular level. The resulting hidrogel/melanin blends appear as flexible hydrophilic materials which, due to the mmelanin component, are slightly colored from yellow to light brown and absorb significantly ultraviolet radiation with cut-off wavelengths between 300 and 380 nanometres, and also the violet, blue and a part of green regions of the visible radiation, to the extent that transmission is 40 to 70% at 500 nanometers and beyond.

The new acquired absorptive properties render the polymer and the ocular devices thereof photoprotective, since the radiation wavebands filtered off are particularly those which can damage the retina in aphakic persons. The absorbing properties are strongly dependent on the synthetic conditions employed in obtaining the hydrogel/melanin blends.

A process that assures the production of such photoprotective polymers according to the present invention can be performed by using aqueous solutions of tyrosine and its related compounds, such as tyramine and synephrine af their maximum possible concentrations or less, at pH 5 to 8, in the presence of oxigen (air) and light at room temperature. In this system, enzymatic catalysis by tyrosinase is necessary in order to catalyze the hydroxylation of monophenols to orthodiphenols. This step is essential in promoting the melanogenesis and could not occur without tyrosinase catalysis. Tyrosinase is a copper-containing enzyme (EC 1.14.18.1) widely distributed in the phylogenetic scale, being responsible for melanization in animals and plants. Tyrosinase is active only in the pH range of 5 to 8, therefore tyrosine and related compounds cannot function as melanin precursors outside this range. To prepare the aforementioned radiation-absorbing polymers and ocular devices, a solution in water of tyrosine or another related compound is prepared and pH is adjusted with buffer solutions at a value between 5 to 8. A hydrogel shaped body or an intraocular lens or an aphakic contact lens, both commercially available, are immersed in the solution, and an appropriate amount of tyrosinase is added. Whitin minutes, the solution becomes pink, and then the coloration intensifies in time passing from red to brown and ending eventually in black. After a certain period of time, according to what degree of absorption is required, the polymeric specimens are removed from the solutions and then subjected to extensive washing in water.

It is also to produce photoprotective polymers according to the present invention by using aqueous solutions of catecholamines at various pH values in the presence of oxygen (air) and light at room temperature. With catecholamines, the catalysis by tyrosinase is effective too, at pH 5 to 8, but it is not necessary, since catecholamines readily autoxidize to melanins through the following pathway: orthodiphenol (catecholamine itself); monocyclic ortho-quinone; leuco-aminochrome; aminochrome; 5,6-dihydroxyindole; indole-5,6-quinone; melanins. Tyrosinase can catalyze only the step from ortho-diphenol to ortho-quinone, and the global gain in the acceleration of the process is not significant.

Extreme pH values are not suitable for the production of photoprotective hydrogels from catecholamine according to the present invention. In strong acidic media (pH less than 3), the production of melanins takes place very slowly or not at all. In strong alkaline media (pH higher than 12), the production of melanins is rapid but they are soluble in the alkaline solution and are easily washed out from the hydrogel matrix. Besides, both strong acids and strong alkaline bases can attack chemically the polymeric substrates and affect adversely their properties. With the alkaline solution, there is also the danger that traces of alkaline hydroxides are retained in the polymers even after extensive washing in water, which excludes their use as ocular biomaterials.

At pH 3 to 6, the aqueous solutions of catecholamines are easily autoxidized in air to melanins, as happens in dilute solutions of common strong acids, such as hydrochloric acid, in which the catecholamines are readily dissolved. When buffer solutions or weak acids are used to provide the range of pH 3 to 6, the solubility of catecholamines is lower and decreases towards higher pH values, but still the production of melanins takes place satisfactorily, even in the presence of some undissolved amounts of catecholamines. The reaction rates are lower as compared to those in the media prepared by dilution of pure acids.

At intermediate pH (6 to 8), the solubility of catecholamines as free bases is very low, which commonly prevents the formation of significant color because the amount of melanins is too low. Therefore, to perform suitable melanogenesis at this pH range, the catecholamines are firstly dissolved in hydrochloric acid, then neutalized with an aqueous solution of ammonium hydroxide. Finally, if necessary, the pH is adjusted to a required value with adequate buffer solutions. In these conditions, catecholamines undergo very easy autoxidation with development of colored melanin pigments.

At basic pH (8 to 12) catecholamines undergo autoxidation generally faster than at neutral pH. The reaction rate and the amount of melanin are dependent on the catecholamines concentration. In very dilute solutions of alkaline hydroxides the autoxidation is faster than in buffer solutions. When alkaline hydroxides are used, the resulting polymeric specimens must be very thoroughly washed and extracted in water in order to remove completely any trace of alkali.

According to the present invention, a hydrogel shaped body or an intraocular lens or an aphakic contact lens are immersed in an aqueous solution of a catecholamine having a certain pH between 3 and 12. After a period of time which varies broadly with the conditions and materials employed, the coloration starts to develop from pink to dark brown. The process is quenched by removing the hydrogel specimen at any time required, commonly not less than 6 hours and not longer than 20 days.

A requirement of the present invention is that the low molecular weight intermediate products occurring in the process of oxidative polymerization, which did not polymerize or they polymerized to a low extent with the formation of extractable oligomers, to be removed from the polymer network prior to the use of the polymeric blend hydrogel/melanin. These indole-type intermediates and their oxidation products, as well as their oligomers may be deleterious to the eye tissues by irritating and toxic effects. Their removal is performed by extraction in water for a variable number of days, with frequent water exchanges, until a steady state is reached in which the rate of extraction is very low, preferably zero, and constant. The content of extractables is determined spectrometrically form the absorption spectra of the water extracts recorded over the range 300 to 500 nanometers. The time required for a polymeric specimen to reach the steady state depends on the type of substrates (hydrogel and melanin precursors) and on the extent of autoxidation process. For a higher efficacy the extraction can be performed in boiling water.

2. The Substrates

Any 4-hydroxyphenylethylamines or catecholamines, with unsubstituted phenolic hydroxyl groups, are suitable for use as melanin precursors according to the present invention. Some specific examples of melanin precursors, most of them available as sympathomimetic drugs, are listed below:

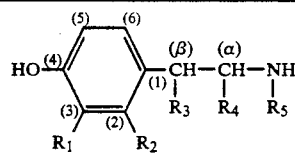

| Rational name | Alternative name | Structure | | | | |
| --- | --- | --- | --- | --- | --- | --- |
| | | $R_1$ (3) | $R_2$ (2) | $R_3$ ($\beta$) | $R_4$ ($\alpha$) | $R_5$ (N) |
| 4-Hydroxyphenylethylamine | Tyramine | H | H | H | H | H |
| 4-Hydroxyphenyl-N-methylamine | | H | H | H | H | $CH_3$ |
| $\beta$-(4-Hydroxyphenyl)-$\alpha$-methylethylamine | Hydroxyamphetamine; Paredrine | H | H | H | $CH_3$ | H |
| $\beta$-(4-Hydroxyphenyl)-$\beta$-hydroxy-N-methylethylamine | Synephrine | H | H | OH | H | $CH_3$ |
| $\beta$-(4-Hydroxyphenyl)alanine | Tyrosine | H | H | H | COOH | H |
| $\beta$-(3,4-Dihydroxyphenyl)ethylamine | Dopamine; 3-Hydroxytyramine | OH | H | H | H | H |
| $\beta$-(3,4-Dihydroxyphenyl)-$\alpha$-methylethylamine | 3-Hydroxy-$\alpha$-methyltyramine | OH | H | H | $CH_3$ | H |
| $\beta$-(3,4-Dihydroxyphenyl)-N-methylethylamine | Epinine | OH | H | H | H | $CH_3$ |
| $\beta$-(3,4-Dihydroxyphenyl)-N-[(2'-methyl-3'-p-hydroxyphenyl)propyl]ethylamine | Dobutamine | OH | H | H | H | a |
| $\beta$-(3,4-Dihydroxyphenyl)-$\alpha$-hydroxyethylamine | Noradrenaline; | OH | H | OH | H | H |

-continued

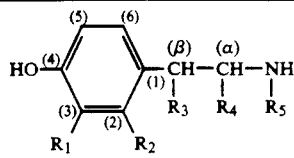

|  |  | Structure | | | | |
|---|---|---|---|---|---|---|
| Rational name | Alternative name | R₁ (3) | R₂ (2) | R₃ (β) | R₄ (α) | R₅ (N) |
| β-(3,4-Dihydroxyphenyl)-β-hydroxy-α-methylethylamine | Norepinephrine; Arterenol α-Methylnoradrenaline; Nordefrin; Corbasil | OH | H | OH | CH₃ | H |
| β-(3,4-Dihydroxyphenyl)-β-hydroxy-α-ethylethylamine | α-Ethylnoradrenaline; | OH | H | OH | C₂H₅ | H |
| β-(3,4-Dihydroxyphenyl)-β-hydroxy-N-methylethylamine | Epinephrine; Adrenaline | OH | H | OH | H | CH₃ |
| β-(3,4-Dihydroxyphenyl)-β-methoxy-N-methylethylamine |  | OH | H | OCH₃ | H | CH₃ |
| β-(3,4-Dihydroxyphenyl)-β-ethyoxy-N-methylethylamine |  | OH | H | OC₂H₅ | H | CH₃ |
| β-(3,4-Dihydroxyphenyl)-β-hydroxy-N-isopropylethylamine | N-isopropylnoradrenaline; isoproterenol; Aleudrine | OH | H | OH | H | CH(CH₃)₂ |
| β-(3,4-Dihydroxyphenyl)-β-hydroxy-N-(2'-hydroxyethyl)ethylamine | N-(β-hydroxyethyl)-noradrenaline | OH | H | OH | H | CH₂CH₂OH |
| α-Methyl-β-(3,4-dihydroxyphenyl)-β-hydroxy-N-methylethylamine | 3,4-Dihydroxyephedrine | OH | H | OH | CH₃ | CH₃ |
| α-Methyl-β-(3,4-dihydroxyphenyl)-β-hydroxy-N-ethylethylamine | 3,4-Dihydroxyhomoephedirine | OH | H | OH | CH₃ | C₂H₅ |
| α-Methyl-β-(3,4-dihydroxyphenyl)-β-hydroxy-N-isopropylethylamine | Isoetharine | OH | H | OH | C₂H₅ | CH(CH₃)₂ |
| β-(3,4-dihydroxyphenyl-2-methyl)-β-hydroxyethylamine | 2-Methylnoradrenaline | OH | CH₃ | OH | H | H |
| β-(2,3,4-Trihydroxyphenyl)ethylamine |  | OH | OH | H | H | H |
| β-(3,4-Dihydroxyphenyl-2-methoxy)ethylamine |  | OH | OCH₃ | H | H | H |
| β-(3,4-Dihydroxyphenyl)alanine | Dopa | OH | H | H | COOH | H |
| β-(3,4-Dihydroxyphenyl)alanine ethyl ester | Dopa ester | OH | H | H | COOC₂H₅ | H |
| β-(3,4-Dihydroxyphenyl)-N-methylalanine | N-Methyldopa | OH | H | H | COOH | CH₃ |
| β-(3,4-Dihydroxyphenyl)-N-methylalanine ethyl ester | N-Methyldopa ester | OH | H | H | COOC₂H₅ | CH₃ |
| β-(3,4-Dihydroxyphenyl-2-methylalanine |  | OH | CH₃ | H | COOH | H | a —CH(CH₃)(CH₂)₂—C₆H₅OH(p)

The list is not limitative since any other derivative with alkyl substituents at the positions 5, 6, α, β and N may also be used, as well as their alkyl ammonium salts with common protic acids.

As to polymeric substrates, any of the hydrogels used to make soft hydrophillic intraocular lenses and aphakic contact lenses are suitable materials that can be used as matrices for autoxidative polymerizations leading to melanin pigments. A hydrogel is a term known in the art and includes homopolymers and copolymers resulted from various monomers and additives. The particular monomers and additives, such as crosslinking agents and polymerization initiators, do not constitute a part of the present invention. Representative of the polymers useful in conjunction with the melanin precursors of the present invention are:

a. Polymers which are derived from 2-hydroxyethyl methacrylate (HEMA), and crosslinked with ethylene glycol dimethacrylate or other methacrylates of particular polyols. A preferred material is poly(2-hydroxyethyl methacrylate), slightly crosslinked with ethylene glycol dimethacrylate, henceforth designated as poly(-HEMA).

b. Polymers which are derived from other hydroxylated methacrylates and acrylates, such as 2-hydroxyethyl acrylate, 2-hydroxypropyl methacrylate and acrylate, glycerol methacrylates and acrylates, and many other well known in the art, as such or mixtures thereof, crosslinked with polyfunctional methacrylates and acrylates or with divinyl benzene derivatives or with other crosslinking agents known in the art.

c. Copolymers of 2-hydroxyethyl methacrylate with aliphatic methacrylates or acrylates such as methyl methacrylate or other members of the homologue series, crosslinked with any of the agents known in the art.

d. Copolymers of 2-hydroxyethyl methacrylate with 2-alkoxyethyl methacrylates or acrylates, such as 2-ethoxyethyl methacrylate, crosslinked with any of the agents known in the art.

e. Polymers and copolymers derived from acrylamide derivatives and N-vinylpyrrolidone, and various combinations thereof, with hydroxylated methacrylates and acrylates, crosslinked with any of the agents known in the art.

However, the list is not limitative since any water-absorbable polymer having a microporous structure may function as a host for the artificial melanogenesis. Also any intraocular lens and aphakic contact lens made from the aforementioned polymers, available commercially or in inventory, or already prescribed to the patient, may be used as a matrix in the method according to the present invention. Except in conjunction with their use as substrates in the method of the invention, the aforementioned ocular devices per se do not constitute a part of this invention.

It is also a feature of this invention to incorporate ultraviolet-absorbing into the hydrogels, either by physical addition or by chemical bonding, which are both practices well known to those skilled in the art. Preferred absorbers are copolymerizable ortho-hydroxybenzophenones and ortho-hydroxyphenyl-2H-benzotriazoles, as disclosed, for example in U.S. Pat. Nos. 3,162,676; 3,313,866; 3,399,173; 3,493,539; 4,260,768; 4,278,589; 4,278,590; 4,304,895; 4,310,650; 4,390,676 and 4,528,311, and in Brit. Pat. No. 885,986, and Belg. Pat. No. 629,109. The incorporation of ultraviolet absorbers imparts absorptive properties to the polymer matrix at wavelengths between 350 to 400 nanometers. Such properties may result also from a prolonged melanogenesis process alone, but there are two disadvantages as compared to the use of ultraviolet absorbers: (a) the cutoff wavelengths are at lower values; (b) the resulting hydrogel/melanin blends are too deeply colored due to a high content in melanin pigments.

Except in combination in the photoprotective polymeric devices of this invention, the particular ultraviolet-absorbing agent or agents per se do not constitute a part of this invention.

The invention will be described in further details and illustrated by way of a few specific examples embodying the method of this invention. The examples are set forth for the purpose of illustration and any specific exposition of details contained therein should not be interpreted as a limitation on the case except as indicated in the appended claims.

EXAMPLE 1

HEMA with a residual content of ethylene glycol dimethacrylate of 0.35% by weight was used to produce buttons of poly(HEMA). HEMA (220 g) was mixed with 335 microliters ethylene glycol dimethacrylate, as a crosslinking agent, and 0.22 g azo-bis-isobutyronitrile, as an initiator, was added and dissolved in said mixture. To achieve complete dissolution, the mixture was ultrasonicated for 20 minutes at room temperature. For polymerization, 2.5-ml aliquots were dispensed in polypropylene moulds enclosed in a sealable moulding system. The moulding system was closed, purged with nitrogen, sealed, and placed in a water bath. Polymerization was carried out following a temperature program starting at 30° C. and ending at 85° C., with a total duration of 30 hours. The buttons were then removed from moulds and cured for 3 hours at 110° C. Poly(HEMA) disks having a diameter of 14 mm and a thickness of 0.75 mm were cut from the buttons, and finely polished.

A poly(HEMA) nonhydrated disk, was placed in an uncovered glass beaker, in which 3 ml of epinephrine-based preparation was added. The beaker was placed in a well lit position. The commercially available Epifrin ® (Allergan Pharmaceuticals) which is a solution 1% by weight epinephrine hydrochloride in water, having pH 3, with some preserving additives, was used. Within two days, the solution became pink and then the color became darker. After 10 days, both the liquid phase and the poly(HEMA) disk were brown. The disk was removed from the solution, rinsed thoroughly with distilled water, and, using a spectrophotometer, the transmission spectrum in the ultraviolet and visible regions, from 250 to 500 nanometers, was plotted in FIG. 1 (curve B) in comparison with a spectrum of a poly(HEMA) disk of the same thickness which was stored in pure water for the same length of time (curve A), both disks in hydrated state. The melanin-pigmented disk was then stored for 28 days in distilled water and occasionally the liquid phase was exchanged for fresh amouts of water. The spectrum was recorded again after this period (curve C). Due to extraction by water of some low molecular weight intermediate products, which absorb in the ultraviolet region, the transmittance below 300 nanometers was higher after extraction in water; at the same time, the transmission of near ultraviolet and visible radiation was lower, presumably due to further advancement of melanin production. A different poly(HEMA) disk was kept in Epifrin for 45 days. The spectrum recorded following this treatment (curve D) shows substantial enhancement of the absorption in both ultraviolet and visible regions.

EXAMPLE 2

HEMA with a residual content of ethylene glycol dimethacrylate of 0.35% by weight was used to produce buttons of poly(HEMA). In 114 g HEMA, 0.114 g azo-bis-isobutyronitrile, as an initiator, and 1.14 g 4-(2'-acryloyloxyethoxy)-2-hydroxybenzophenone, as a copolymerizable ultraviolet absorber, were dissolved using an ultrasonic bath for 20 minutes. The homogeneous mixture was polymerized following the procedure of Example 1. Poly(HEMA) disks, with a diameter of 14 mm and a thickness of 1 mm were cut from the buttons and finely polished. The disks were hydrated for 2 days in distilled water and then placed in uncovered beakers containing 5 ml portions of epinephrine at various concentrations obtained by diluting Epifrin 1%. Concentrations used were 0.3, 0.7 and 1% by weight. The disks were kept in the corresponding solutions for 9 days when the solution became brown. They were then rinsed and stored in distilled water for 20 days, with 3 water exchanges performed during this period. Their transmittance curves between 250 and 500 nanometers were then recorded and it was noticed that the variation of epinephrine concentration did not induce difference in the transmission, which was 31% at 400 nanometers, 46% at 450 nanometers, and 54% at 500 nanometers. The cutoff wavelength, as determined mainly by the presence of the ultraviolet absorber, was 375 nanometers.

EXAMPLE 3

Figure 2:
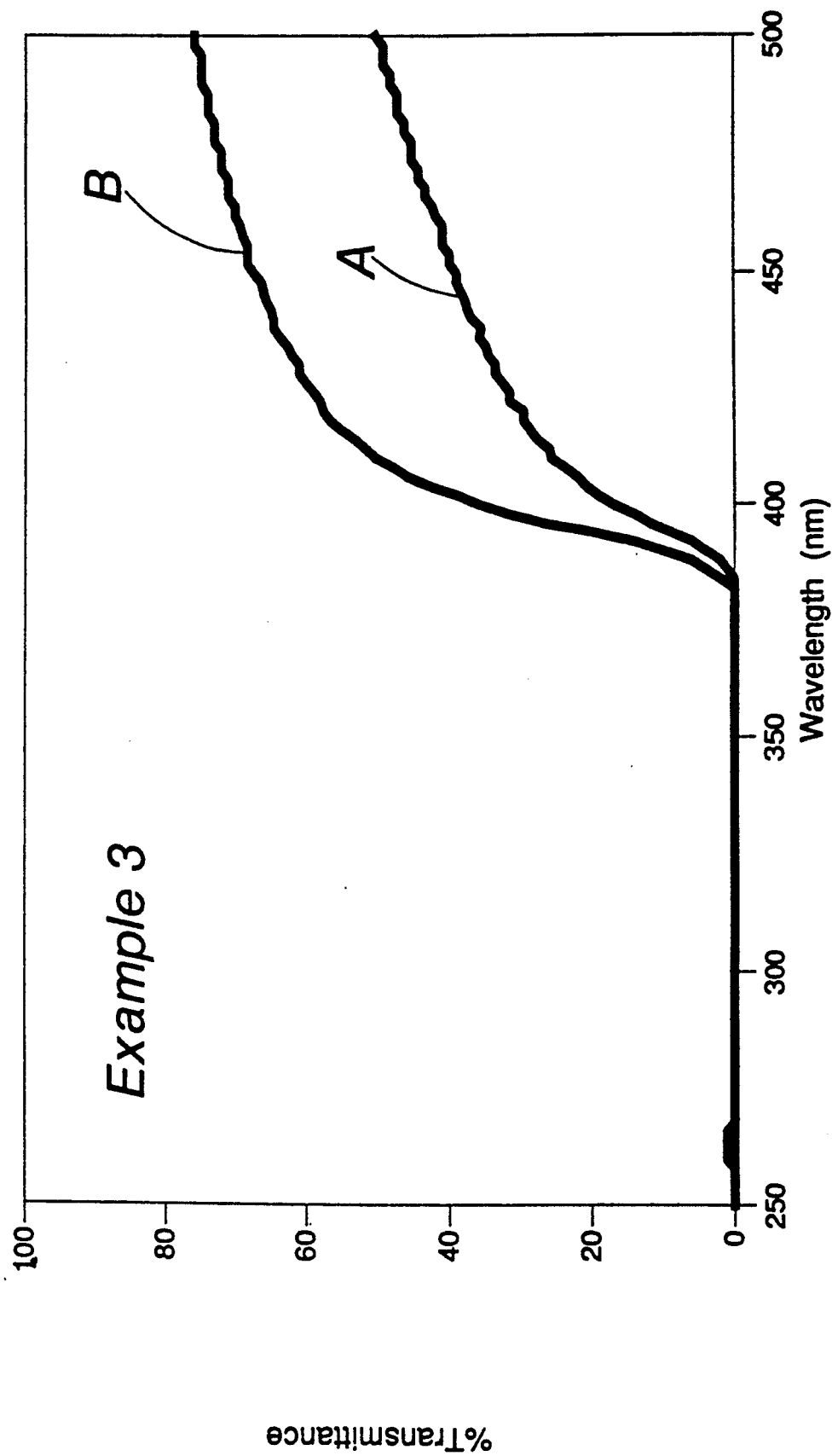
FIG. 2 is a plot of transmittance for the polymer compositions of Example 3.

Azo-bis-isobutyronitrile (0.03 g), as an initiator, and 0.15 g Tinuvin ® 213 (CIBA-Geigy), as an additive ultraviolet absorber, were dissolved in 30 g HEMA which had a residual content of ethylene glycol dimethacrylate of 0.35% by weight. Tinuvin 213 is the product of transesterification between methyl 3-[3'-(2H-benzotriazol-2-yl)-5'-tertbutyl-4'-hydroxyphenyl]propionate and polyethylene glycol 300. The mixture was polymerized following the procedure of Example 1. Poly(HEMA) disks with a diameter of 10 mm and a thickness of 1 mm were cut from the buttons and finely polished. In an experiment, a disk was extracted in distilled water for 70 days with weekly water exchanges. In another experiment, a disk was kept in 3 ml Epifrin 1% for 6 days, until the liquid acquired a brown color. The disk was removed from the epinephrine solution and extracted in distilled water for 64 days with weekly water exchanges. At the end of these periods, the transmittance curves of the hydrated disks from both experiments were recorded as in FIG. 2. Both poly(HEMA)

disks exhibited the same cutoff wavelength (384 nanometers), due to the presence of the benzotriazole ultraviolet absorber. The transmission of the remaining radiation was substantially lower in the melanin-pigmented poly(HEMA) (curve A) than in the untreated poly(HEMA) (curve B).

EXAMPLE 4

Figure 3:
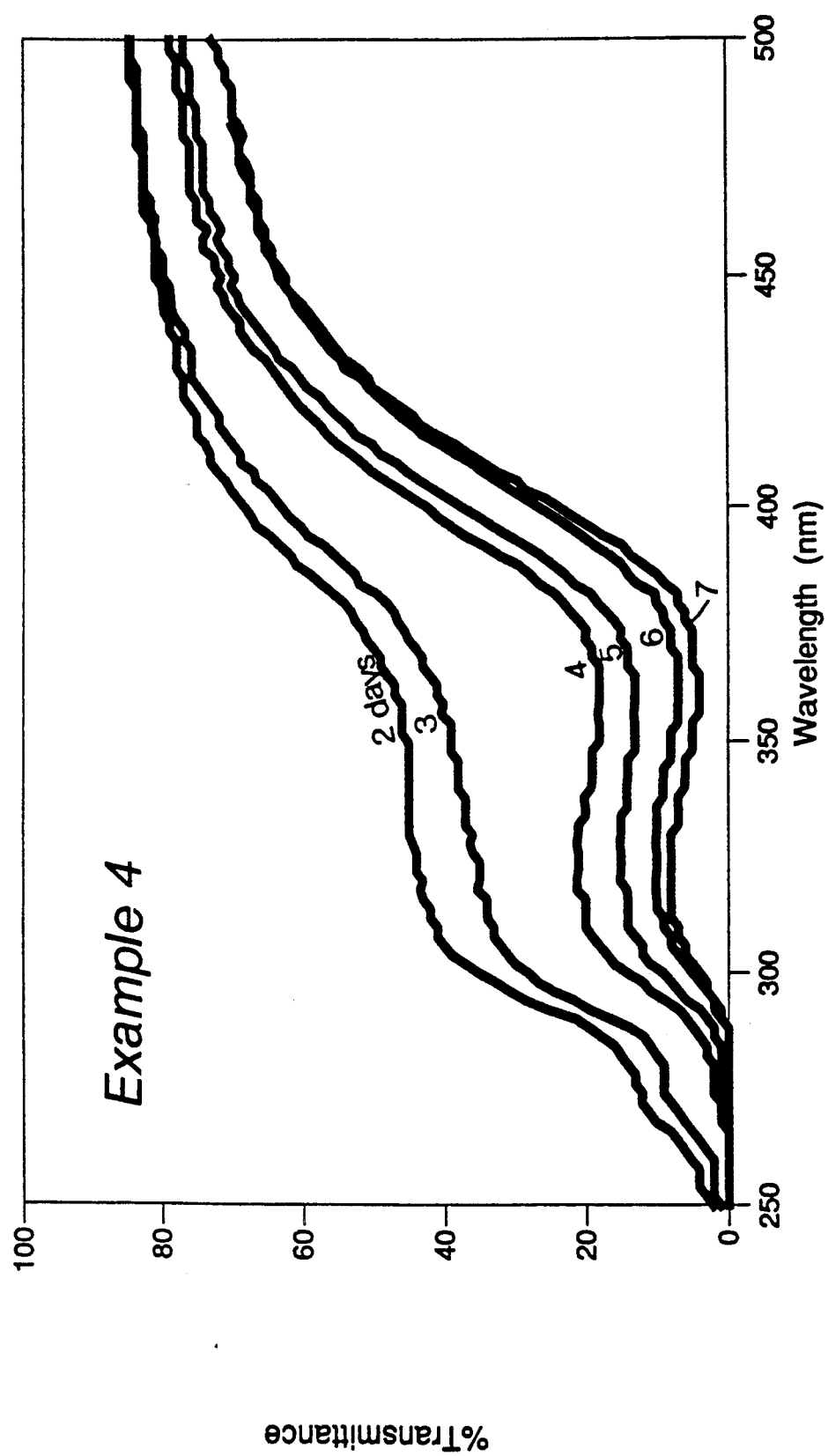
FIG. 3 is a plot of transmittance for the polymer compositions of Example 4, which were subjected to different durations of artificial melanogenesis.
Figure 4:
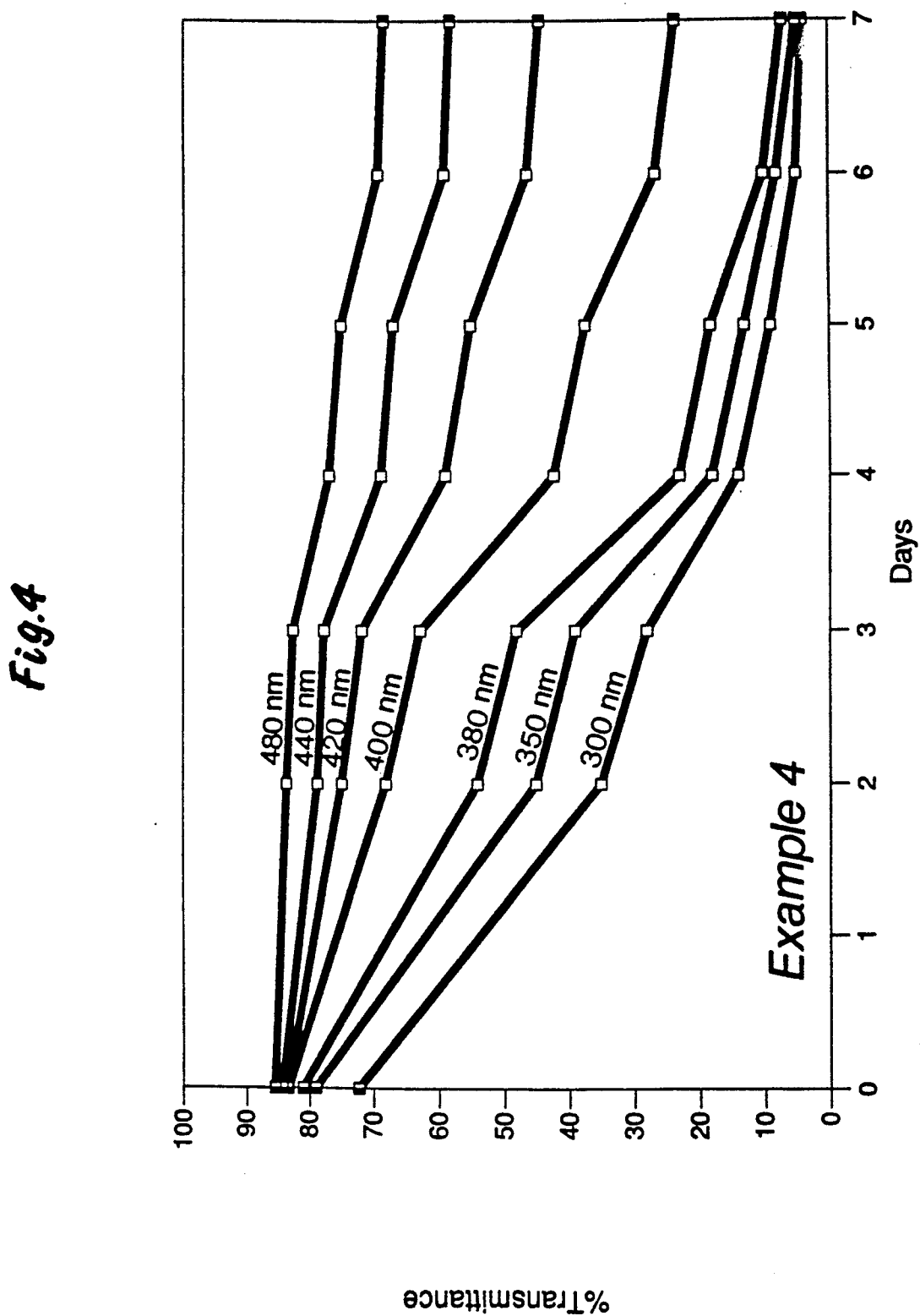
FIG. 4 is a plot of variation of transmittance of the polymer compositions of Example 4, at different representative wavelengths, as a function of melanogenesis duration.

Commercially available double-trimmed poly(HEMA) buttons, with a diameter of 14 mm and a thickness of 4 mm, were individually subjected to pigmentation in 5-ml portions of Epifrin 1% for various durations from 2 to 7 days. After their successive removal from the reaction media, each button was extracted in distilled water for 6 days with daily water exchanges. The buttons were then dried in a vacuum oven for 3 days, and cut into disks of 10-mm diameter and 0.8-mm thickness, and finely polished. The transmittance curves of all disks, in dry state, plotted from 250 to 500 nanometers, as in FIG. 3, show a direct correlation between duration of the melanogenesis and radiation-absorptive properties of the pigmented materials. FIG. 4 is a plot of the transmittance at a few wavelengths in near ultraviolet and visible regions, as a function of the duration of melanogenesis.

The same disks after hydration exhibited slightly lower absorption in ultraviolet; however the absorption was substantially unchanged in the visible region.

When the materials were firstly hydrated and then subjected to pigmentation, the final absorptive properties were improved in the visible region, but not in the ultraviolet region.

EXAMPLE 5

Figure 5:
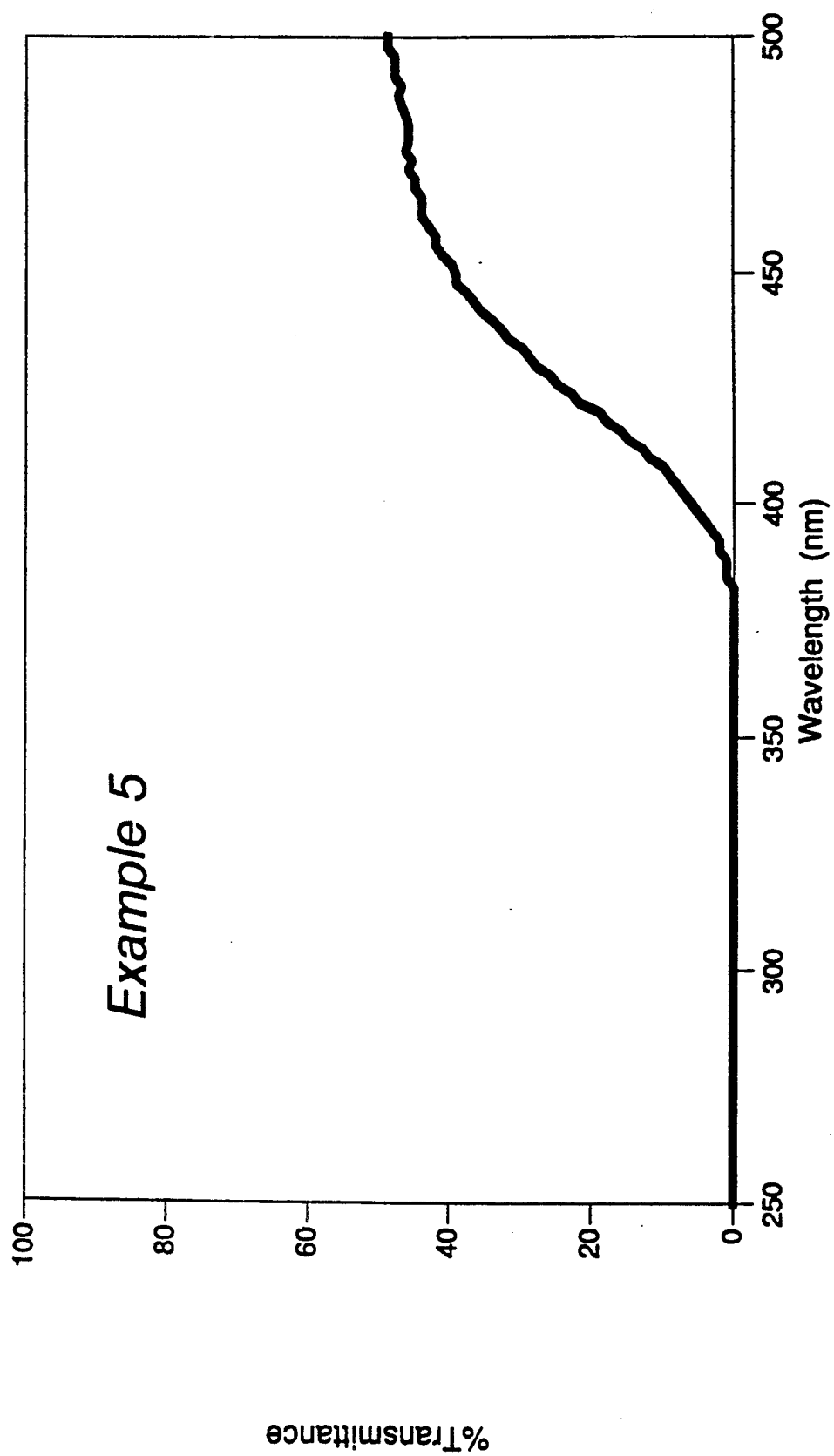
FIG. 5 is a plot of transmittance for the polymer composition of Example 5.

A commercially available double-trimmed poly(HEMA) button, with a diameter of 12.5 mm and a thickness of 5 mm was hydrated to equilibrium for 9 days, with periodical water exchanges. The button was then immersed in 5 ml Epifrin 1% where it was kept for 20 days, until is acquired a dark brown color. The pigmented button was then extracted in distilled water for 6 days, with daily water exchanges and dried in a vacuum oven for 3 days. The hard button was cut into a disk, 10-mm diameter and 0.8 mm thickness and finely polished. FIG. 5 plots the transmittance of this disk in a dry state. The photoprotective properties are very good, with a cutoff wavelength at 382 nanometers, and transmittances of 5.9% at 400 nanometers, 38.8% at 450 nanometers and 48.5% at 500 nanometers.

EXAMPLE 6

Figure 6:
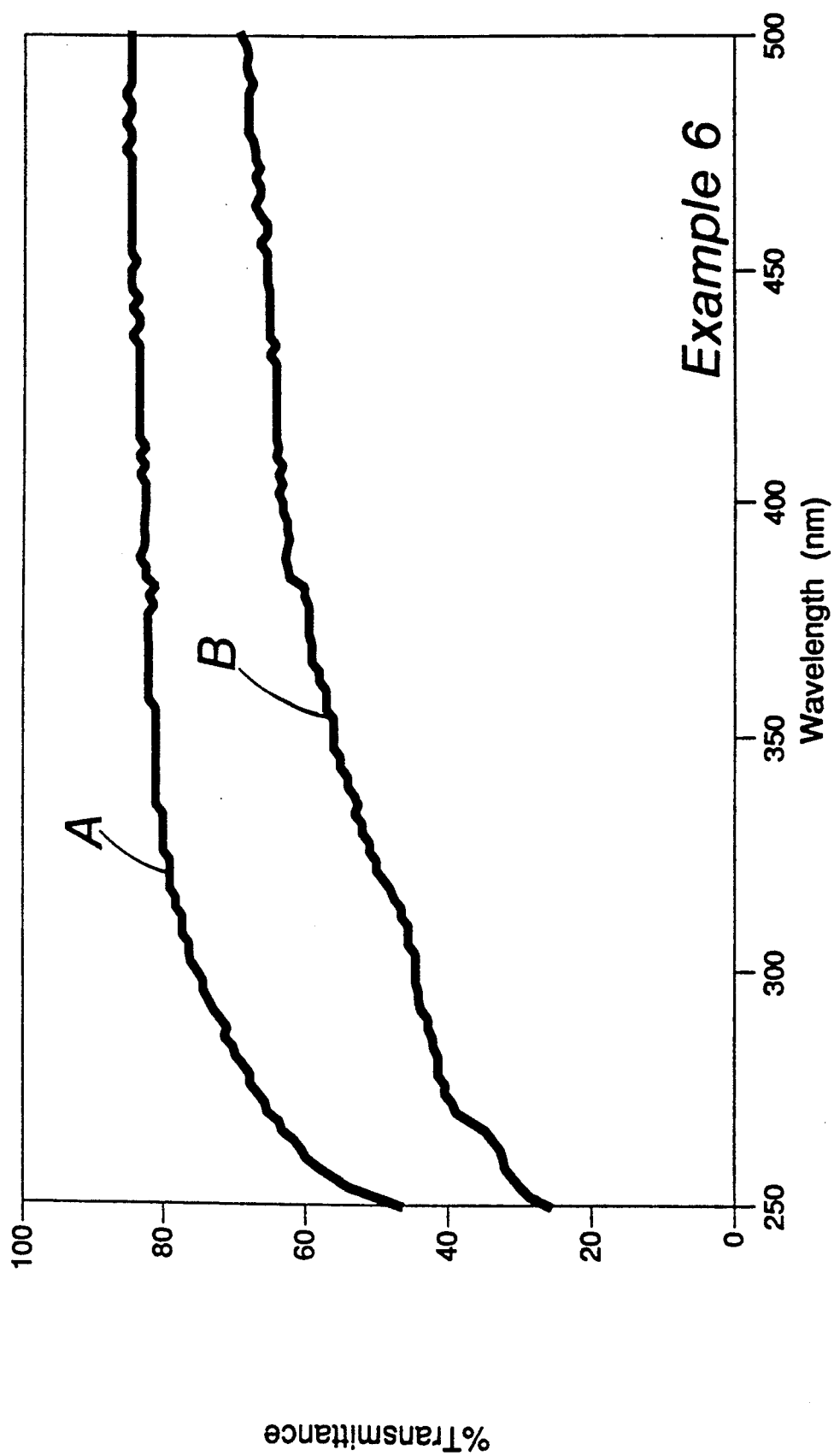
FIG. 6 is a plot of transmittance of an IOGEL TM intraocular lens before and after treatment in epinephrine, in accordance with Example 6.

A commercially available hydrogel (polymacon) IOGEL TM intraocular lens was immersed in 10 ml Epifrin 1% where it was kept for 55 hours, when a dark red color was aquired by both solution and lens. The pigmented lens was stored in distilled water for 6 days, with daily water exchanges. FIG. 6 plots the transmittance of the lens before (curve A) and after (curve B) the treatment in eprinephrine solution. Although the duration of treatment was short, the drop in transmission was significant. Since the IOGEL lenses were available only without ultraviolet-absorbing properties, no absorption in this region could be substantially imparted.

EXAMPLE 7

In 1 g HEMA (residual ethylene glycol dimethacrylate 0.30% by weight), 1.5 microliters ethylene glycol dimethacrylate was added, and 0.001 g azo-bis-isobutyronitrile, as an initiator, and 0.03 g 2-[2-hydroxy-4-methacryloyloxy(2'-hydroxy-3'-propoxy)phenyl]-5-chloro-2H-benzotriazole, as a copolymerizable ulraviolet absorber, were dissolved using an ulrasonic bath for 30 minutes. The homogeneous mixture was polymerized following the procedure of Example 1, and a button was obtained. From this button, a disk with a diameter of 10 mm and a thickness of 1.1 mm was cut and then stored in distilled water for 90 days, with periodical water exchanges.

Figure 7:
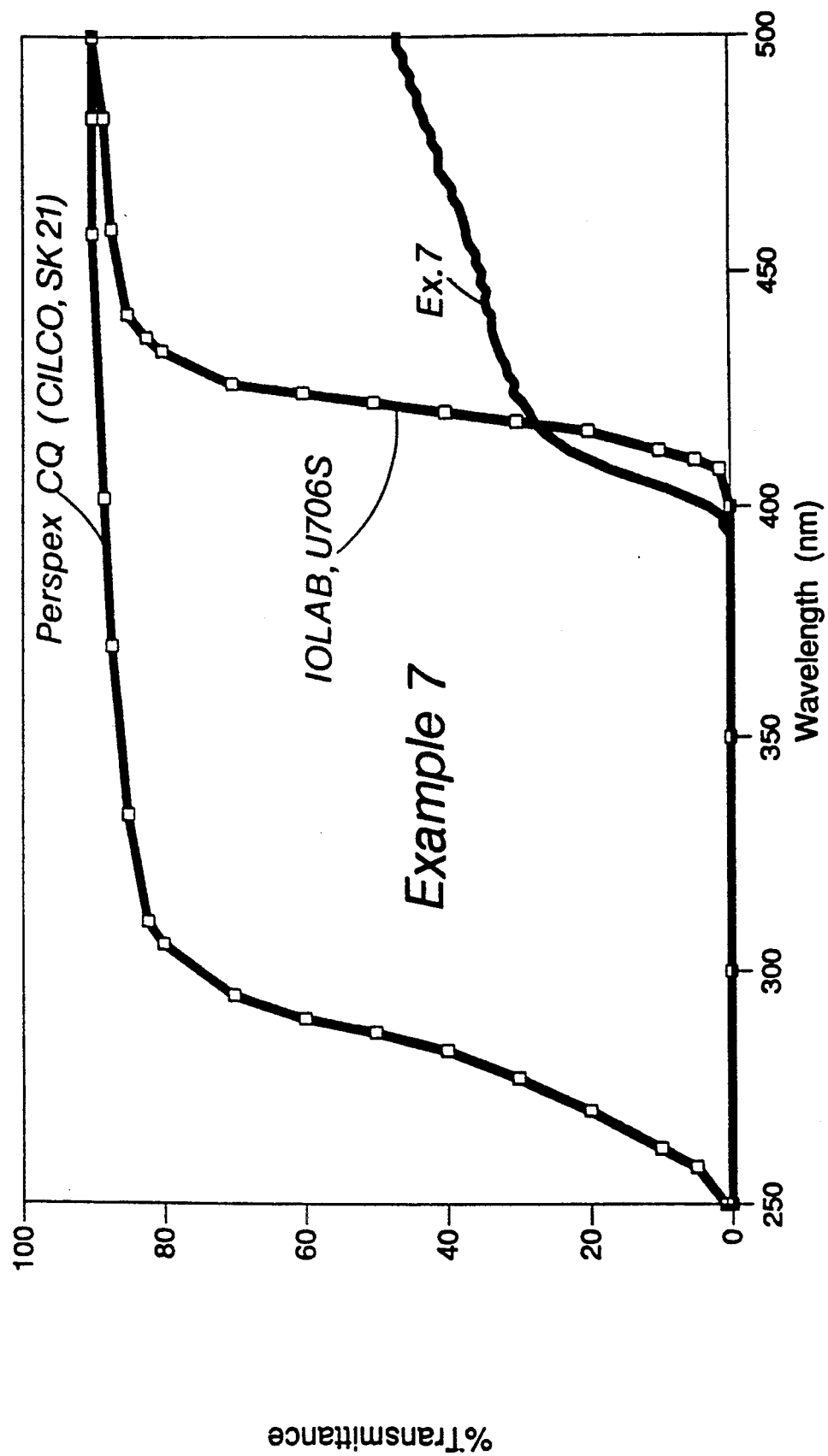
FIG. 7 is a plot of transmittance for the polymer composition of Example 7, as compared with the transmittance curves of two commercial intraocular lenses.
Figure 8:
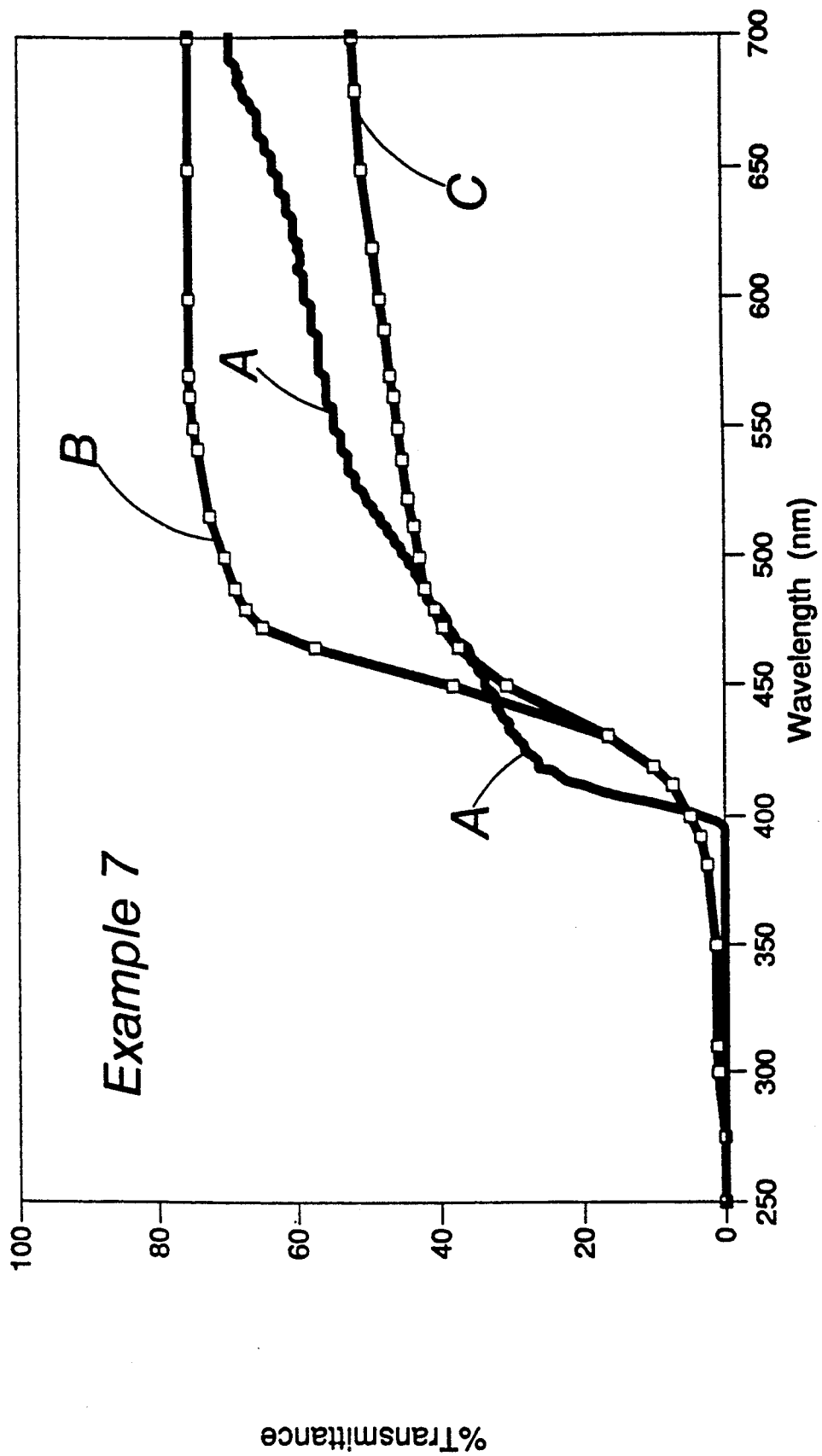
FIG. 8 is a plot of transmittance for the polymer composition of Example 7 up to 700 nanometres, as compared with the transmittance curves of the human natural lens at two different ages.

The hydrated disk was placed in 10 ml Epifrin 1% and removed after 7 days, when it acquired a dark brown color with a green tinge. The disk was extracted in distilled water for 6 days, with daily water exchanges. The transmittance curve of this disk, in hydrated state, was plotted in FIG. 7 (curve A) in comparison with the same curves for commercial poly(methyl methacrylate) nonabsorbing (curve B) and ultraviolet-absorbing (curve C) intraocular lenses, as described in Mainster, M. A., American Journal of Ophthalmology, vol. 102, pp. 727–732 (1986), "The Spectra, Classification, and Rationale of Ultraviolet-Protective Intraocular Lenses". Also, in FIG. 8, the transmittance from 250 to 700 nanometers of the material of this example (curve A) is compared with the transmittance of the natural human lens, at 25 years (curve B), and, respectively, 54 years (curve C) of age, as described in Lerman, S., American Journal of Optometry and Physiological Optics, vol. 64, pp. 11–22 (1987), "Chemical and Physical Properties of the Normal and Aging Lens: Spectroscopic (UV, Fluorescence, Phosphorescence, and NMR) Analyses".

EXAMPLE 8

Azo-bis-isobutyronitrile (0.03 g), as an initiator, and 0.03 g Tinuvin ® P (CIBA-Geigy), as an additive ultraviolet absorber, were dissolved in 30 g HEMA which had a residual content of ethylene glycol dimethacrylate of 0.35% by weight. Tinuvin P is the trade name for 2-(2'-hydroxy-5'-methylphenyl)-2H-benzotriazole. The mixture was polymerized following the procedure of Example 1. A disk with a diameter of 10 mm and a thickness of 1 mm was cut from a button and finely polished. The disk was stored in distilled water for 6 months, with periodical water exchanges. The disk was then immersed in 10 ml solution prepared by dissolving 0.05 g epinephrine in 50 ml aqueous solution 0.01% by weight sodium hydroxide (pH 11), and kept in this solution for 8 days, until the color acquired was dark brown. The disk was extracted in distilled water for 6 days, with daily water exchanges, and then its transmission from 250 to 500 nanometers was plotted. Because the ultraviolet absorber has leached out, the cutoff wavelength was only 300 nanometers. However, due to the presence of melanin pigments, the transmittance was 39.2% at 400 nanometers, 49% at 450 nanometers, and 57.3% at 500 nanometers.

EXAMPLE 9

Epinephrine (0.05 g) was added to 50 ml buffer solution of pH 8 and thoroughly stirred. In 10 ml of the resulting solution, which still may contain undissolved epinephrine, a commercially available double-trimmed poly(HEMA) button with a diameter of 12.5 mm and a thickness of 5 mm, hydrated to equilibrium, was immersed and kept for 6 days until the solution and the hydrogel became dark brown. After removal, the button is extracted in distilled water for 8 days, with daily water exchanges. The hydrogel button was then dried in a vacuum oven for 3 days, and a disk of 10-mm diameter and 0.95-mm thickness was subsequently cut from it. The transmittance curve of the disk in the dry state was plotted between 250 and 500 nanometers. The cutoff wavelength was 290 nanometers, but subsequent transmission was low, being 10% at 380 nanometers and 25.5% at 400 nanometers. Transmission was 61.5% at 450 nanometers and 69.9% at 500 nanometers.

EXAMPLE 10

Epinephrine (0.01 g) is dissolved in 10 ml acetic acid 0.01N with a pH 3.4.

2,2'-Azo-bis(2,4-dimethyl-valeronitrile) (0.0625 g), as an initiator, and 0.652 g 4-(2'-acryloyloxyethoxy)-2-hydroxybenzophenone, as a copolymerizable ultraviolet absorber, were dissolved in a mixture of 62.5 g HEMA, which had a residual content of ethylene glycol dimethacrylate of 0.03% by weight, and 300 microliters ethylene glycol dimethacrylate. The mixture was polymerized using the moulding system of Example 1, but a temperature program starting at 30° C. and ending at 45° C., with a total duration of 40 hours, was used. The buttons were cured for 18 hours at 110° C. A disk having a diameter of 13 mm and a thickness of 1 mm was cut from one button, and then hydrated in distilled water for 6 days with daily water exchanges. The hydrated disk was kept in the aforementioned epinephrine solution for 7 days, until a dark pink coloration was achieved. The disk was then extracted in distilled water for 6 days with daily water exchanges. At the end of this period, the transmittance curve was recorded. The cutoff wavelength was 374 nanometers, and the transmissions at 400, 450, and 500 nanometers were, respectively, 43.6%, 62.1%, and 68.9%.

EXAMPLE 11

Figure 9:
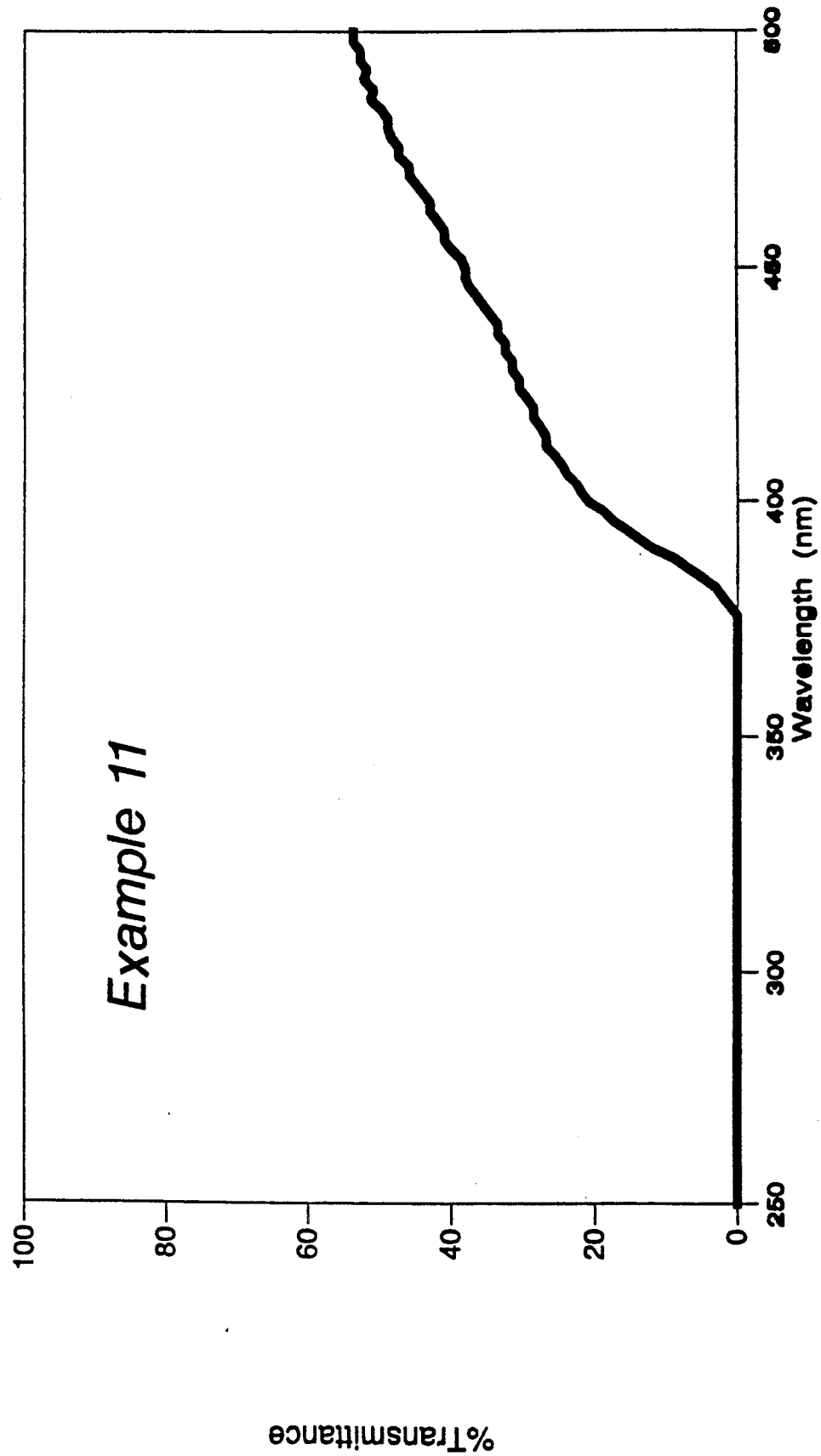
FIG. 9 is a plot of transmittance for the polymer composition of Example 11.

Epinephrine (2 g) was dissolved in 11.5 ml aqueous hydrochloric acid of 3.6% by weight concentration. The solution, which had a brown color, was then carefully neutralized to litmus paper with a solution 1% by weight ammonium hydroxide. After adding 35 ml of the latter solution, a pH 6.45 was measured. A hydrated disk of poly(HEMA) containing 1% by weight bonded benzophenone ultraviolet absorber, prepared following the procedure of Example 10, was immediately immersed in 10 ml neutralized epinephrine solution. Within seconds, the solution was red, and in one hour it became brown. The disk was kept for 3 days in the solution, and then extracted for 6 days in distilled water. Its transmittance curve was plotted in FIG. 9. The cutoff wavelength at 376 nanometers is due to the ultraviolet-absorbing agent, but the presence of melanin pigments is responsible for the low transmission of the visible light from 400 to 500 nanometers.

EXAMPLE 12

Tyrosine (0.2 g) was dissolved in 500 ml hot distilled water by stirring for 2 hours. After cooling, a pH 5.6 was measured. A hydrated poly(HEMA) disk containing 0.5% by weight non-bonded benzophenone ultraviolet absorber, prepared following the procedure of Example 3, was immersed in 10 ml of the aforementioned tyrosine solution, and 0.001 g tyrosinase (Sigma Chemicals Co.), having a tyrosinase activity of 2,200 units per milligram and a catechol oxidase activity of 737,600 units per milligram, was added to the solution. The solution became pink within seconds. After 20 hours, when the solution was very dark and black melanin pigments precipitated, the hydrogel disk was removed and then extracted in distilled water for 6 days, with daily water exchanges. Its spectrum showed a cutoff at 382 nanometers, and transmissions of 38.2% at 400 nanometers, 66.3% at 450 nanometers, and 72.8% at 500 nanometers.

EXAMPLE 13

To 70 ml tyrosine solution, prepared following the procedure of Example 12, 10 ml buffer solution with pH 8 was added, and a pH 7.4 was measured. A hydrated poly(HEMA) disk containing 1% by weight bonded benzophenone ultraviolet absorber, prepared following the procedure of Example 10, was immersed in 10 ml of the aforementioned solution. Tyrosinase (0.001 g), having the same characteristics as in Example 12, was added. After 3 days, when the color acquired was dark red, the hydrogel disk was transferred in distilled water and extracted for 6 days with daily water exchanges. Its spectrum showed a cutoff at 374 nanometers, and transmission of 50% at 400 nanometers, 68% at 450 nanometers, and 72.8% at 500 nanometers.

We claim:

1. A method of making photoprotective soft hydrophilic polymers which absorb radiation in the range of 250 to 700 nanometers to the same extent as the natural lens in the human eye, comprising:
   (a) preparing a hydrophilic polymer specimen substantially based on 2-hydroxyethyl methacrylate;
   (b) preparing an aqueous solution of 4-hydroxyphenylethylamine or forms of 4-hydroxyphenylethylamine having substituents comprising alkyl, hydroxyl, hydroxyalkyl, alkoxy, carboxyl and alkyl esters thereof, or their salts, of 0.01% to 0.5% by weight concentration, having a pH value between 5 and 8;
   (c) Immersing said hydrophilic polymer specimen either in a dry, or a hydrated state, into said solution, using 1 to 5 ml solution for 1 g polymer;
   (d) adding to the said solution, containing the polymer specimen, catalytic amounts of tyrosinase and allowing the process of oxidative polymerization of the 4-hydroxyphenylethylamine-based compound identified in part (b) within the polymer network to take place in the presence of oxygen (air) and light, at room temperature, for durations between 6 hours and 20 days;
   (e) removing said hydrophilic polymer specimen from solution at the end of said process and extracting said polymer specimen in water until the steady state with respect to extractables is achieved.

2. A method of making photoprotective soft hydrophilic polymers which absorb radiation in the wavelength range of 250 to 700 nanometers to the same extent as the natural lens in the human eye, comprising:
   (a) preparing a hydrophilic polymer specimen substantially based on 2-hydroxyethyl methacrylate;
   (b) preparing an aqueous solution of catecholamine and forms of catecholamine having substituents comprising alkyl, hydroxyl, hydroxyalkyl, alkoxy, carboxyl and alkyl esters thereof, or their salts, of 0.01% to 1% by weight concentration, having a pH value between 3 and 12;
   (c) immersing said hydrophilic polymer specimen either in a dry, or a hydrated state, into said solution, using 1 to 5 ml solution for 1 g polymer;

(d) allowing the process of oxidative polymerization of the catecholamine-based compound identified in part (b) within the polymer network to take place in the presence of oxygen (air) and light, at room temperature, for durations between 6 hours and 20 days;

(e) removing said hydrophilic polymer specimen from solution at the end of said process and extracting said polymer specimen in water until the steady state with respect to extractables is achieved.

3. The method as defined in claim 1, wherein said hydrophilic polymer specimen is a hydrogel available for making ocular devices.

4. The method as defined in claim 2, wherein said hydrophilic polymer specimen is a hydrogel available for making ocular devices.

5. The method as defined in claim 1, wherein said hydrophilic polymer specimen is a hydrogel intraocular lens available for use by aphakic persons.

6. The method as defined in claim 2, wherein said hydrophilic polymer specimen is a hydrogel intraocular lens available for use by aphakic persons.

7. The method as defined in claim 1, wherein said hydrophilic polymer specimen is a hydrogel aphakic contact lens available for use.

8. The method as defined in claim 2, wherein said hydrophilic polymer specimen is a hydrogel aphakic contact lens available for use.

9. A method for preparing photoprotective hydrophilic polymers based substantially on 2-hydroxyethyl methacrylate which comprises incorporating into said polymer an amount of 4-hydroxyphenylethylamine or catecholamine and forms of 4-hydroxyphenylethylamine or catecholamine having substituents comprising alkyl, hydroxyl, hydroxyalkyl, alkoxy, carboxyl and alkyl esters thereof, or their salts, as a melanin precursor, allowing the process of oxidated polymerization of the 4-hydroxyphenylethylamine- or catecholamine-based compound identified above within the polymer network to take place under polymerization conditions and collecting the resultant polymer that exhibits the property of absorption of radiation in the wave length range of about 250 to 750 nanometers of the spectrum.

10. The method according to claim 9 including the additional step of manufacturing from said resultant polymer an ocular lens suitable for human use.

11. The method according to claim 9 wherein said polymerization is carried out in the presence of oxygen and light.

12. The process according to claim 11 wherein said polymerization is conducted at room temperature for between about 6 hours and 20 days.

13. The method according to claim 12 wherein said polymerization is conducted in the presence of a suitable catalyst at a pH range of about 5 to 8.

14. A photoprotective hydrophilic polymer as prepared according to the method of claim 9.

15. An ocular lens suitable for human use as prepared according to the method of claim 10.

16. A hydrogel intraocular lens according to claim 15 suitable for use by aphakic persons.

* * * * *

UNITED STATES PATENT AND TRADEMARK OFFICE
CERTIFICATE OF CORRECTION

PATENT NO. : 5,252,628
DATED      : October 12, 1993
INVENTOR(S) : Chirila, et al It is certified that error appears in the above-indentified patent and that said Letters Patent is hereby corrected as shown below:

On the Title Page item [45] before the Issue Date insert an "*".

After item [73] the following should be inserted:

[*] Notice:   The portion of the term of this patent subsequent to June 12, 2009, has been disclaimed.

Signed and Sealed this

First Day of February, 1994

Attest:

BRUCE LEHMAN

*Attesting Officer*      Commissioner of Patents and Trademarks